United States Patent
van der Steen et al.

(10) Patent No.: US 11,576,574 B2
(45) Date of Patent: Feb. 14, 2023

(54) METHOD FOR MEASURING A SUBJECT'S EYE MOVEMENT AND SCLERAL CONTACT LENS

(71) Applicant: Erasmus University Medical Center Rotterdam, Rotterdam (NL)

(72) Inventors: Johannes van der Steen, Rotterdam (NL); Johannes Jacob Mient Pel, Rotterdam (NL); Jochem Jesse Visser, Rotterdam (NL)

(73) Assignee: Erasmus University Medical Center Rotterdam, Rotterdam (NL)

( * ) Notice: Subject to any disclaimer, the term of this patent is extended or adjusted under 35 U.S.C. 154(b) by 1097 days.

(21) Appl. No.: 16/301,366

(22) PCT Filed: May 11, 2017

(86) PCT No.: PCT/NL2017/050292
§ 371 (c)(1),
(2) Date: Nov. 13, 2018

(87) PCT Pub. No.: WO2017/196172
PCT Pub. Date: Nov. 16, 2017

(65) Prior Publication Data
US 2019/0274543 A1    Sep. 12, 2019

(30) Foreign Application Priority Data

May 13, 2016    (EP) .................................... 16169545

(51) Int. Cl.
*A61B 3/113*       (2006.01)
*G02C 7/04*        (2006.01)
(Continued)

(52) U.S. Cl.
CPC .............. *A61B 3/113* (2013.01); *A61B 3/145* (2013.01); *A61B 5/1127* (2013.01); *A61B 90/39* (2016.02);
(Continued)

(58) Field of Classification Search
CPC ......... A61B 3/113; A61B 90/39; A61B 3/145; A61B 5/1127; G02B 1/043; G02C 7/043
(Continued)

(56) References Cited

U.S. PATENT DOCUMENTS

2003/0223037 A1    12/2003  Chernyak
2007/0177103 A1     8/2007  Migliaccio et al.
(Continued)

FOREIGN PATENT DOCUMENTS

JP    2013-521576 A    6/2013
WO    95/08135 A1      3/1995
(Continued)

OTHER PUBLICATIONS

International Search Report and Written Opinion dated Sep. 22, 2017 in International (PCT) Application No. PCT/NL2017/050292 (10 pages).
(Continued)

*Primary Examiner* — James R Greece
(74) *Attorney, Agent, or Firm* — McDermott Will & Emery LLP

(57) ABSTRACT

Method and contact lens (3) for measuring a subject's three dimensional eye movement including torsional movement. A video camera (1) is provided for recording an image of the subject's eye (2). The contact lens (3) is provided for placement over the subject's eye (2). The contact lens (3) comprises one or more markers (3a,3b) that are detectable by the video camera (1) and are positioned at a lateral offset (D) with respect to a central part (3p) of the contact lens (3).
(Continued)

The one or more markers (3a,3b) are configured for detecting torsional rotation (R) of the subject's eye (2) around a line of sight axis (C) of the subject's eye (2) by using the video camera (1) to track a position of the one or more markers (3a,3b).

17 Claims, 4 Drawing Sheets

(51) Int. Cl.
    *A61B 90/00*     (2016.01)
    *A61B 3/14*     (2006.01)
    *A61B 5/11*     (2006.01)
    *G02B 1/04*     (2006.01)

(52) U.S. Cl.
    CPC ............ *G02B 1/043* (2013.01); *G02C 7/043* (2013.01); *A61B 2090/3904* (2016.02); *A61B 2090/397* (2016.02); *G02C 7/046* (2013.01)

(58) Field of Classification Search
    USPC ................................ 351/200, 205, 206, 219
    See application file for complete search history.

(56) References Cited

U.S. PATENT DOCUMENTS

2012/0281181 A1     11/2012     Chen et al.
2016/0007849 A1     1/2016     Krueger

FOREIGN PATENT DOCUMENTS

| WO | WO-9508135 A1 * | 3/1995 | ............ G02C 7/041 |
| WO | 2008/014085 A2 | 1/2008 | |
| WO | WO-2008014085 A2 * | 1/2008 | ............ A61B 3/113 |
| WO | 2012040196 A1 | 3/2012 | |
| WO | 2016007124 A1 | 1/2016 | |

OTHER PUBLICATIONS

International Preliminary Report on Patentability dated Nov. 22, 2018 in International (PCT) Application No. PCT/NL2017/050292 (8 pages).

JPO—1st Examination Report for related Japanese Appln. No. JP 2018-559917 dated Mar. 8, 2021, including English machine translation retrieved on Apr. 15, 2021 from <www.j-platpat.inpit.go.jp/p0200>, on 6 pgs total.

* cited by examiner

METHOD FOR MEASURING A SUBJECT'S EYE MOVEMENT AND SCLERAL CONTACT LENS

RELATED APPLICATIONS

This application is a United States National Phase under 35 U.S.C. § 371 of International Application No. PCT/NL2017/050292 filed on May 11, 2017, which claims priority to European Patent Application No. 16169545.7, filed May 13, 2016, both of which are hereby incorporated by reference in their entirety for all purposes.

TECHNICAL FIELD AND BACKGROUND

The present disclosure relates to a method for measuring a subject's eye movement, in particular a video-based method to track three-dimensional (3D) eye movement, i.e. horizontal, vertical and torsional movement. The disclosure also relates to a scleral contact lens for measuring the subject's eye movement.

Precise measurement of eye movements can be an important tool to provide direct and indirect assessment of vestibular, oculomotor, visual, and neurologic function. Currently, 3D eye movement is predominantly measured with either with (i) a scleral search coil method or (ii) a video-based (infrared) three-dimensional eye tracking device.

The scleral search coil method is based on the use of coils that are embedded into a tightly-fitting contact lens or a rubber ring that adheres to the eye. In animal studies, the scleral search coil may be surgically implanted into the sclera of the eye. Alternating magnetic fields are generated by magnets positioned around the eye. Through electromagnetic induction, electric currents are generated in the search coils. The polarity and amplitude of the current generated varies with the direction and angular displacement of the eye. By measuring these values, the position of the eye can be determined.

Video based systems typically use a small camera and digital image processing hardware and software to compute the eye's position and movement. The torsion component of eye movement may in principle be measured with the use of video-oculography, e.g. by using of iris landmarks or identifying and tracking stable iris features that stand out in the video signal. However, this may require features that are not always present or obvious. In addition, such a method is likely to produce false torsional estimates when there are irregular changes in pupil shape during the recording. Another solution involves the use of an artificial paint marker that is applied directly on the sclera of the eye and is tracked. A disadvantage is that such a marker quickly fades on the moist sclera surface and it is quite an invasive procedure as well.

These two methods of scleral search coils and video-oculography were compared in a scientific article of the Van der Steen group (Houben et al., Invest Ophthalmol Vis Sci. 47(1):179-87 (2006)). In the article it was concluded that a high degree of correlation existed between the measurement of horizontal and vertical eye position signals with both systems. However, the measurement of torsional movement was significantly different. Although video-based infrared three-dimensional eye tracking systems are largely replacing scleral search coil systems, torsional movement of the eye is difficult to measure with a video-based infrared three-dimensional eye tracking system due to problems in tracking the eye ball around the visual axis based on identification of an iris signature.

Accordingly, further improvements in the measurement of 3D eye movement, especially torsional eye movement, with a video-based infrared three-dimensional eye tracking device are desired.

SUMMARY

Some aspects of the present disclosure relate to a method for measuring a subject's eye movement. A contact lens is provided for placement over the subject's eye and a video camera, typically infrared, is provided for recording an image of the subject's eye with the contact lens. The contact lens comprises one or more markers that are detectable by the video camera. The one or more markers are positioned at a lateral offset with respect to a central part of the contact lens. The central part is in use positioned over a pupil of the subject's eye. The one or more markers are configured for detecting torsional rotation of the subject's eye around a line of sight axis of the subject's eye by using the video camera to track a position of the one or more markers.

Accordingly, images may be recorded of the subject's eye while wearing the contact lens. A coordinate, e.g. angle, of the torsional rotation can be calculated based on a position of the one or more markers in the recorded images since they are positioned at a lateral offset with respect to a central part (where the pupil is). For example, an image processor may receive images from the video camera. The image processor can be programmed, e.g. with image recognition software, for tracking a relative or absolute position of the one or more markers. The image processor may calculate a coordinate of the torsional rotation of the subject's eye. For example, the coordinate of the torsional rotation can be calculated by comparing a position of one or more markers relative to each other and/or a position of the pupil in the subject's eye. It will be appreciated that the pupil itself can be used as a marker of the line of sight axis.

Additionally, by painting the contact lens with a ring-shaped opaque area surrounding a transparent central part, an outside part of the subject's pupil may be masked. The transparency of the central part may allow the subject to still view through the contact lens while the area will appear dark or black to the video camera because of the subject's pupil that is (in use) located behind the transparent area. The partial masking of the pupil may provide the effect that a change in pupil size is "hidden" from the camera. This may advantageously stabilize the video signal for accurate assessment of the eye movement. In particular, the video-based eye tracker may detect a constant pupil diameter which can make the signal to noise ratio independent from lighting conditions (which affect the pupil size). Markers placed on the ring may provide stable and trackable features that can be more easily identified using software for assessment of torsional movement of the eye.

Under bright lighting conditions, the pupil diameter is typically between two to four millimetres. To prevent the pupil being smaller than the mask, it is preferable to provide the transparent central part with a diameter less than four millimetres. Under low lighting conditions the pupil diameter is typically between four to nine millimetres. To still mask the maximum pupil, it is preferably to provide the opaque surrounding ring shape with an outer diameter of more than five millimetres, preferably more than eight millimetres, e.g. one centimetre, e.g. covering the whole iris. Alternatively, or in addition, to still mask the minimum pupil, it is preferably to provide the opaque surrounding ring shape with an inner diameter of less than four millimetres, preferably more than three millimetres.

For reliable recognition it is preferred that the markers are painted on the contact lens against a clear or contrasting background. By providing, the markers in the opaque area, a consistent background color can be guaranteed, e.g. a marker having a color that is contrasting with the background of the opaque area. Circular shaped markers may be preferable because these remain the same under rotation and can be recognized more consistently in the recorded image. Preferably the markers are formed by dark, e.g. black, pigmented spots. For example it may be desirable that the markers have more than eighty percent absorption, e.g. in a visible or infrared wavelength range, depending on the light source. Generally, markers may also be formed by contrasting shapes and colors as long as the markers are recognizable by the camera and image processor.

To accurately track the position of the markers it is desired that each marker is isolated, i.e. surrounded by the background. Accordingly, the markers are preferably isolated from each other and/or isolated from the pupil. In this way they may be individually identifiable by the video camera to track individual positions of each of the markers. By keeping the markers relatively close to the centre, they may be visible also when the subject's eye is moved around. For example, the markers are disposed in a corneal area around the pupil of the subject's eye, e.g. overlapping the area of the subject's iris.

Various types and setups can be used for the camera. By using an infrared camera, images can be recorded with less or no dependence on the lighting conditions. Optionally, an infrared light source can be provided, e.g. on the camera or elsewhere, to enhance visibility of the contact lens and markers. By providing the video camera on spectacles or glasses the video camera can be worn on the subject's head and keep a constant view of the subject's eye. Alternatively, a video camera can also be disposed on another type head-worn device, e.g. head band or helmet. By providing the head-worn device with a semi-transparent window, the video camera need not be in direct view of the user and record the image of the subject's eye via the window. Alternatively, the video camera can also be set up separate from the subject, e.g. recording the subject's whole face and processing the part where the subject's eye is located.

Further advantages may be achieved by the aspects of a scleral contact lens for measuring a subject's eye movement. The scleral lens may provide rotational stability with respect to the eye compared to e.g. soft lenses. Rotational stability may be even better using a toric scleral lens. For example, the scleral lens can be painted with a ring-shaped opaque area surrounding a transparent central part of the contact lens. The opaque area is disposed to partly cover an outside ring area of a subject's pupil to mask the outside ring area of the subject's pupil from a video camera to portray the pupil with a constant diameter to the video camera, independent of lighting conditions. The opaque area may be provided with one or more contrasting markers to determine torsion of the subject's eye.

BRIEF DESCRIPTION OF DRAWINGS

These and other features, aspects, and advantages of the apparatus, systems and methods of the present disclosure will become better understood from the following description, appended claims, and accompanying drawing wherein:

DESCRIPTION OF EMBODIMENTS

Figure 1A:
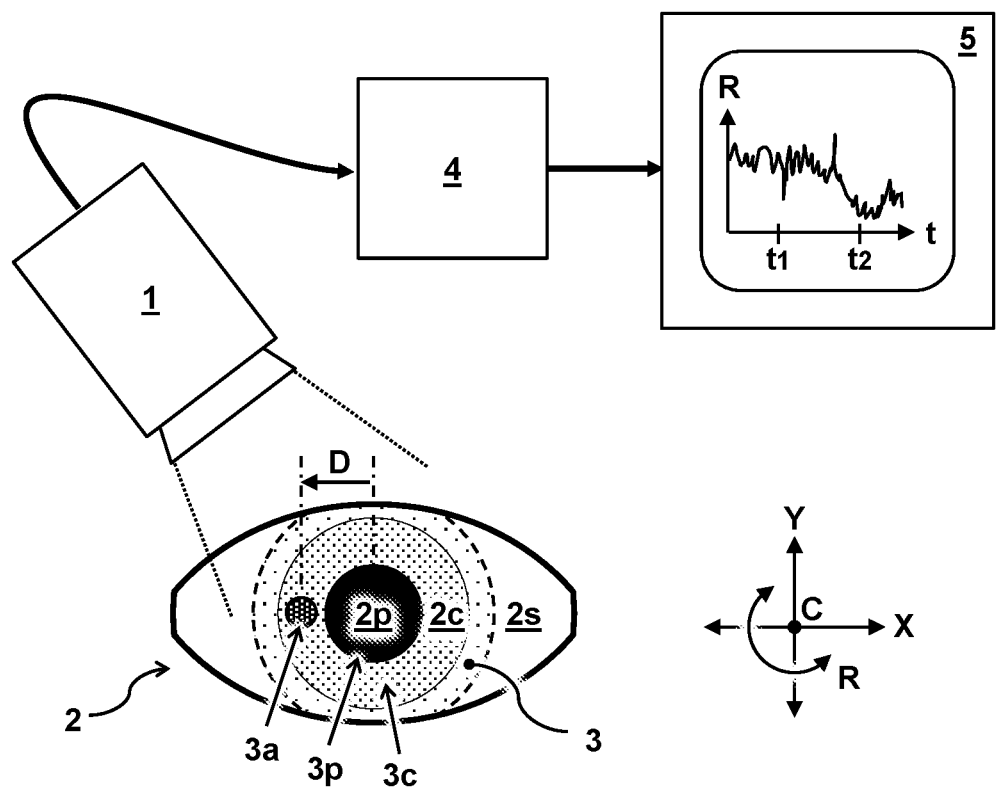
FIG. 1A schematically shows a method for measuring a subject's eye movement.

In some instances, detailed descriptions of well-known devices and methods may be omitted so as not to obscure the description of the present systems and methods. Terminology used for describing particular embodiments is not intended to be limiting of the invention. As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features. It will be further understood that when a particular step of a method is referred to as subsequent to another step, it can directly follow said other step or one or more intermediate steps may be carried out before carrying out the particular step, unless specified otherwise.

The invention is described more fully hereinafter with reference to the accompanying drawings, in which embodiments of the invention are shown. In the drawings, the absolute and relative sizes of systems, components, layers, and regions may be exaggerated for clarity. Embodiments may be described with reference to schematic and/or cross-section illustrations of possibly idealized embodiments and intermediate structures of the invention. In the description and drawings, like numbers refer to like elements throughout. Relative terms as well as derivatives thereof should be construed to refer to the orientation as then described or as shown in the drawing under discussion. These relative terms are for convenience of description and do not require that the system be constructed or operated in a particular orientation unless stated otherwise.

FIG. 1A schematically shows a method for measuring a subject's eye movement.

In one embodiment, the method comprises providing a video camera 1 for recording an image of the subject's eye 2. In another or further embodiment, the method comprises providing a contact lens 3 for placement over the subject's eye 2.

The contact lens 3 comprises one or more markers 3a that are detectable by the video camera 1 and are positioned at a lateral offset D with respect to a central part 3p of the contact lens 3. The central part 3p is in use positioned over a pupil 2p of the subject's eye. The one or more markers 3a are configured for detecting torsional rotation R of the subject's eye 2 around a line of sight axis C of the subject's eye 2 by using the video camera 1 to track a position of the one or more markers 3a.

In one embodiment, the method includes recording images of the subject's eye 2 and calculating a coordinate, e.g. angle, of the torsional rotation R based on a position of the one or more markers 3a, in the recorded images. For example, an image processor 4 may be configured to receive images from the video camera 1. In some embodiments, the image processor 4 is programmed with image recognition software for tracking a relative or absolute position of the one or more markers 3a. For example, the image processor 4 is configured to calculate a coordinate of the torsional rotation R of the subject's eye 2. In one embodiment, the coordinate of the torsional rotation R is calculated by comparing a position of a marker 3a to a position of a pupil 2p of the subject's eye 2. Alternatively, or in addition, the torsion may be calculated by comparing the positions of multiple markers with respect to each other and/or the pupil 2p.

In one embodiment, the coordinate of the torsional rotation R is calculated by comparing a position of the one or more markers at a first time t1 to a position of the one or more markers at a second time t2. For example, rotation of the eye can be detected by a change in the relative position of a marker with respect to the pupil and/or with respect to a second marker.

Figure 1B:
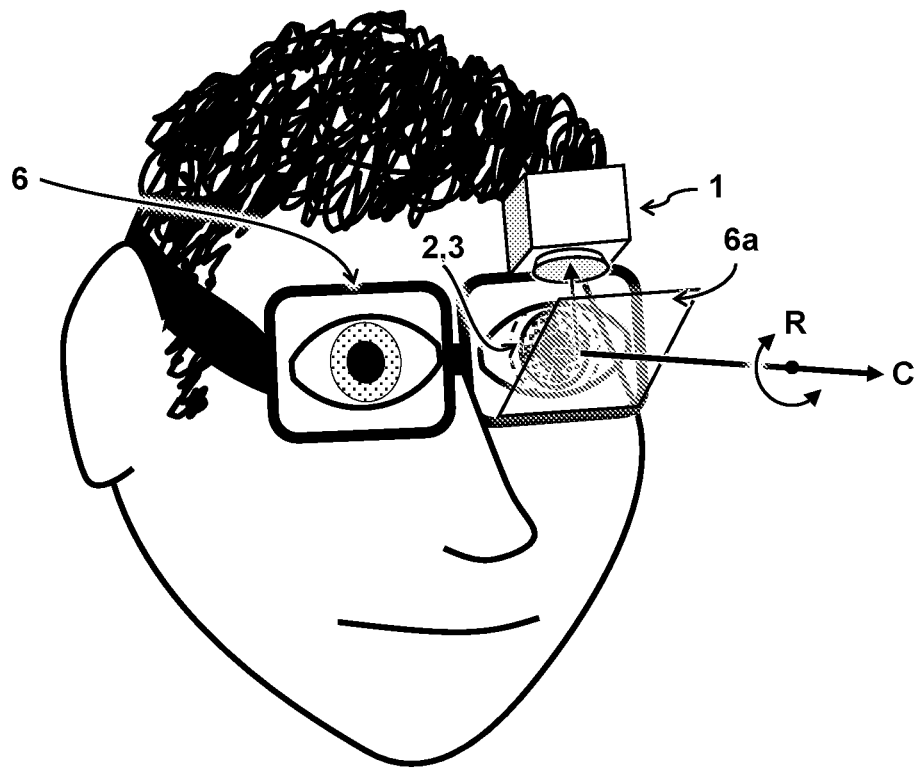
FIG. 1B schematically shows an embodiment of a video camera mounted on spectacles worn by a user.

FIG. 1B schematically shows an embodiment wherein the video camera 1 is disposed on spectacles 6 for wearing the video camera 1 on the subject's head.

In some embodiments, the spectacles comprises a semi-transparent window 6a tilted at an angle for the video camera 1 to record the image of the subject's eye 2 via the semi-transparent window 6a. The video camera 1 can also be disposed on another type head-worn device, e.g. head band or helmet not shown. Alternatively, the video camera 1 can also be set up separate from the subject, e.g. recording the subject's whole face and processing the part where the subject's eye 2 is located. Preferably, the video camera 1 is an infrared camera, optionally including an infrared light source. In one embodiment, markers on the contact lens have more than eighty percent absorption in an infrared wavelength range, e.g. in a range of the infrared light source.

To assess function or health of the subject, it can be useful to measure and/or calculate a torsional range of the subject's eye. For example, the torsional range is calculated based on a maximum and minimum coordinate of the torsional rotation R. This may be determined e.g. by having the subject tilt his head while viewing an image and measuring a minimum or maximum coordinate of the torsional rotation R.

Figure 2A:
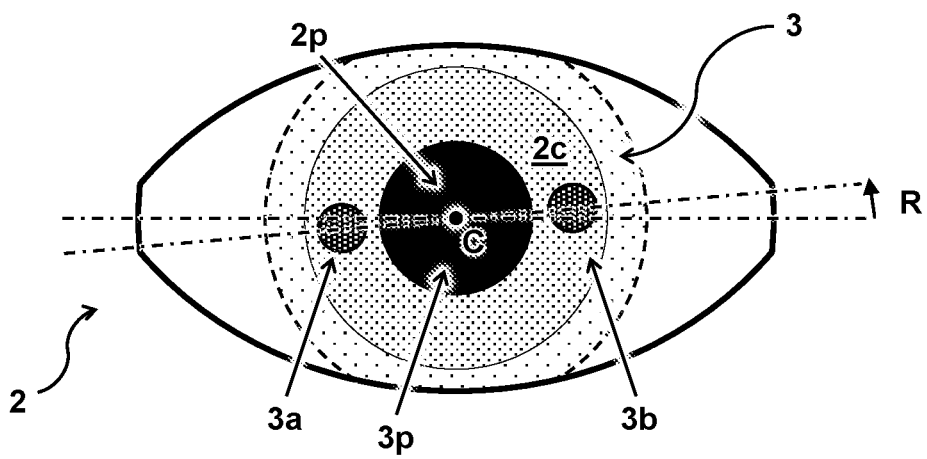
FIG. 2A schematically shows an embodiment of a clear contact lens having markers.

FIG. 2A schematically shows an embodiment of a clear contact lens 3 placed in the subject's eye 2.

The contact lens has markers 3a,3b which contrast with the background, in this case the color of the iris. In one embodiment, the one or more markers 3a,3b are disposed in a corneal area 2c around the pupil 2p of the subject's eye 2, e.g. overlapping the area of the subject's iris, keep them in the infrared vision field during horizontal and vertical eye movements.

In one embodiment, the one or more markers 3a,3b are formed by dark, e.g. black, spots. For example, the one or more markers 3a,3b are painted on the contact lens 3 against a clear or contrasting background, reliable recognition. Preferably, the one or more markers 3a,3b have a circular shape. This may provide a neutral form that doesn't change during rotation of the eye in contrast e.g. to an 'X' or triangular shape.

In one embodiment, the one or more markers 3a,3b are isolated from each other and/or isolated from the pupil 2p for being individually identifiable by the video camera 1 to track individual positions of each of the markers. In some embodiments, the coordinate of the torsional rotation R is calculated by comparing a position of a first marker 3a to a position of a second marker 3b. For example, the coordinate of the torsional rotation R is calculated based on an angle between a first marker 3a to a position of a second marker 3b with respect to a reference angle, e.g. previous measured angle, horizontal angle, et cetera. Preferably, a pair of markers 3a,3b is positioned on a line at opposite sides of a central transparent part 3p of the contact lens 3 corresponding to the pupil 2p.

Figure 2B:
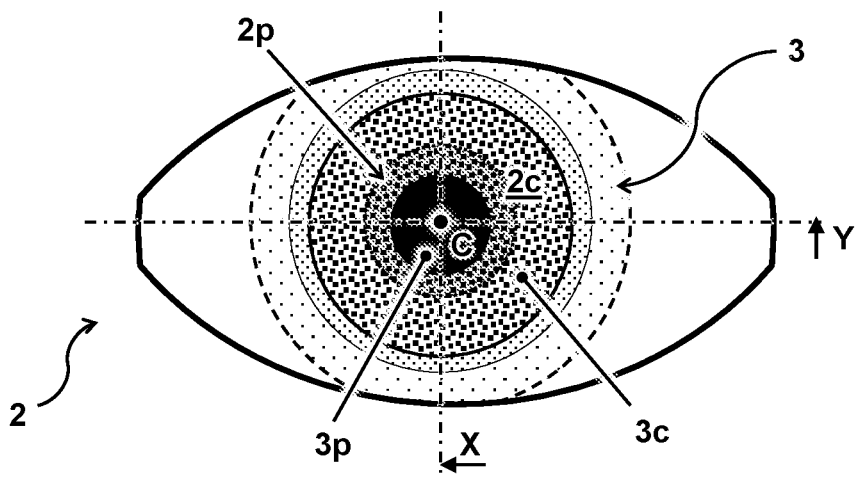
FIG. 2B schematically shows an embodiment of a contact lens having an opaque area to mask a diameter of the pupil.

FIG. 2B schematically shows an embodiment a contact lens having an opaque area 3c to mask a diameter of the pupil 2p.

In one embodiment, the contact lens 3 is painted with a ring-shaped opaque area 3c surrounding a transparent central part 3p. Preferably the opaque area 3c is disposed to partly cover an outside ring area of a subject's pupil 2p to mask the outside ring area of the subject's pupil 2p from the video camera (not shown here). In this way, the subject's pupil 2p may be portrayed with a constant shape and/or diameter to the video camera. In another or further embodiment, a diameter of the transparent central part 3p, defined by the surrounding ring-shaped opaque area 3c, is less than four millimetres, preferably less than three, e.g. two millimetres. In another or further embodiment, an outer diameter of the surrounding ring-shaped opaque area 3c, is more than five millimetres, preferably more than eight millimetres, e.g. one centimetre.

In some embodiments, the opaque area 3c is painted with a color that is contrasting to that of the subject's pupil 2p for the video camera 1 to distinguish between the painted ring-shaped opaque area 3c and the subject's pupil 2p. For example, a light color can be used to paint the ring-shaped area 3c. Preferably, one or more markers 3a,3b are formed in the opaque area 3c.

Figure 2C:
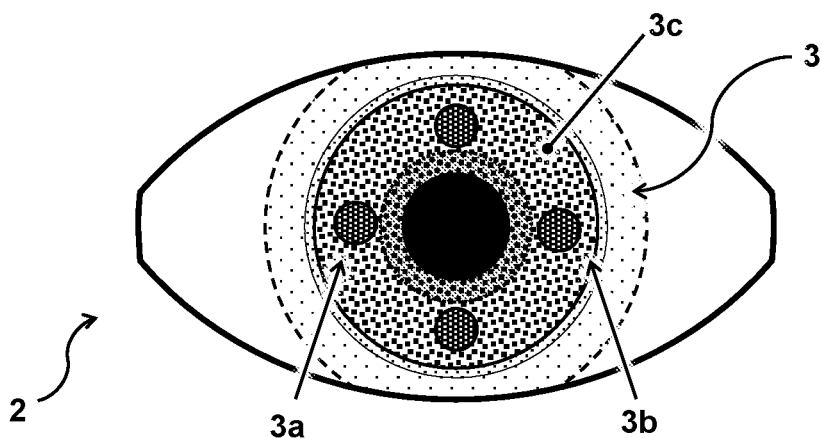
FIG. 2C schematically shows an embodiment of a contact lens having an opaque area and markers.

FIG. 2C schematically shows an embodiment of a contact lens having both an opaque area 3c and markers 3a,3b. Preferably more than two markers are provided, e.g. four or more. Preferably, the markers are distributed equidistantly around the pupil. In some methods, multiple references of pairs of markers may be tracked.

Figure 3A:
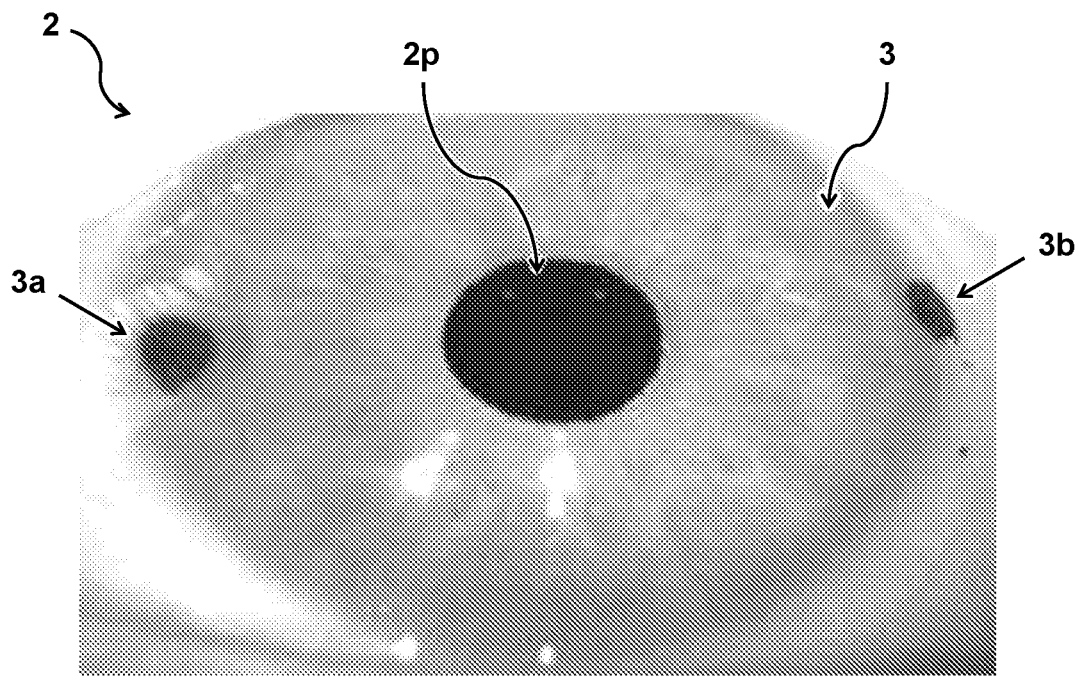
FIG. 3A shows a photo of a soft contact lens having painted markers.

FIG. 3A shows a photo of a soft contact lens having painted markers.

Figure 3B:
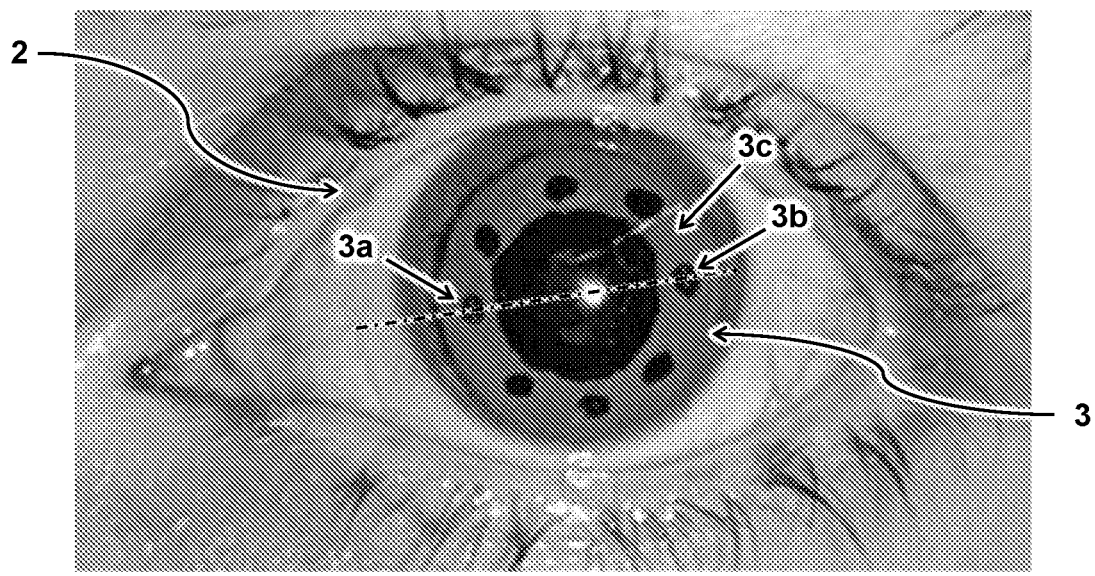
FIG. 3B shows a photo of a scleral lens having an opaque area and markers.

FIG. 3B shows a photo of a scleral lens having an opaque area and markers.

In principle, a soft contact lens can be used to apply landmarks on the eye and track them to quantify torsional movement, e.g. using infrared video-glasses. Accordingly, in some embodiments, the contact lens is a soft contact lens having one or more dark spots e.g. applied with a permanent marker. A disadvantage of the use of this kind of lens is its characteristic to float on the eye. When the subject keeps the eye open, lens changes into a different position. Also the hydrophilic material of the lens has been found unsuitable to mark with waterproof ink, obviously the combination of lacrimal fluid and blinking were making the ink wash out within a too short period of time.

The scleral lens is a large diameter hard contact lens that has its resting point lateral of the limbus (border of the cornea and sclera) of the eye. In contrast to a normal contact lens that floats on the eye, a scleral lens has a tight fit on the eye over the cornea and can be worn without discomfort for several hours. It does no harm to the eye and can even be used to cure or protect the eye in some medical cases. This type of lens is often subscribed for optical correction of an irregular corneal surface (e.g. Keratoconus). 125 years ago the first scleral lenses were made of glass blown shells. The introduction of moulding for glass lenses and the introduction of plastics like PMMA were important steps for the improvement of these lenses. Oxygen permeable lenses were found in 1983, which was of importance for ocular health. Due to the introduction of smaller hard corneal lenses and the soft lens scleral lens development stopped for a while. Since several years, new developments have led to a revival: improved manufacturing, lower costs, better designs, greater reproducibility and computerised imaging of ocular topography. Indications for scleral lenses vary from visual improvement, corneal protection to cosmetic and sport purposes.

Preferably, the ring covers the sclera and part of the iris in such way that the edge of the pupil, i.e. the inner-iris border, is covered by the imprint of the scleral lens, in the light as well as in the dark. Thus, the pupil can still be detected by a video-based eye tracker, the patient is able to see through the lens, but pupil size changes cannot be seen or detected. Enlargement of the pupil, i.e. increasing the sclera-iris diameter, occurs behind the imprinted ring. One advantage is that the video-based eye tracker always detects one pupil diameter which makes signal to noise ratio independent from lighting conditions. This very specific feature of the painted lens also solves another recently described problem in infrared eye tracking, namely that of jittering of the inner-iris border (i.e. pupil outer diameter) causing postsaccadic oscillations in the eye signal after ending a saccade. In the shown embodiment, the opaque area is provided with two rings around the central area: a black painted inner ring that that appears dark in infra-red light just like the pupil does. This ring is surrounded by a light-coloured outer ring, e.g. red, provided with dark (pigmented) markers. Alternatively, or in addition, the painted inner ring may be extended to completely cover the pupil, i.e. form a painted inner circle. For example the inner circle may absorb in an infrared wavelength range of the camera to hide the pupil in its recorded image. For example the painted inner circle may be at least partially transparent for visible light to allow a user to look through while appearing opaque to the camera.

In one embodiment, the contact lens is a scleral contact lens, e.g. with a diameter between twelve and twenty-five millimetre. In another or further embodiment, the contact lens 3 is a corneo-scleral or mini-scleral contact lens with a diameter between twelve and eighteen millimetre. These and other aspects of the present disclosure may be embodied by various scleral contact lenses for measuring a subject's eye movement.

For example, as shown in FIG. 3B, the contact lens is painted with a ring-shaped opaque area surrounding a transparent central part of the contact lens, which central part is in use positioned over a pupil of the subject's eye. The opaque area is disposed to partly cover an outside ring area of a subject's pupil to mask the outside ring area of the subject's pupil from a video camera to portray the pupil with a constant diameter to the video camera. In some embodiments, the opaque area is painted with a color that is contrasting to that of the subject's pupil for the video camera to distinguish between the painted ring-shaped opaque area and the subject's pupil. In other or further embodiments, one or more markers are formed in the opaque area wherein the one or more markers are detectable by the video camera and are positioned at a lateral offset with respect to the central part. As explained above, the one or more markers, are configured for detecting torsional rotation of the subject's eye around a line of sight axis of the subject's eye by using the video camera to track a position of the one or more markers.

Figure 4:
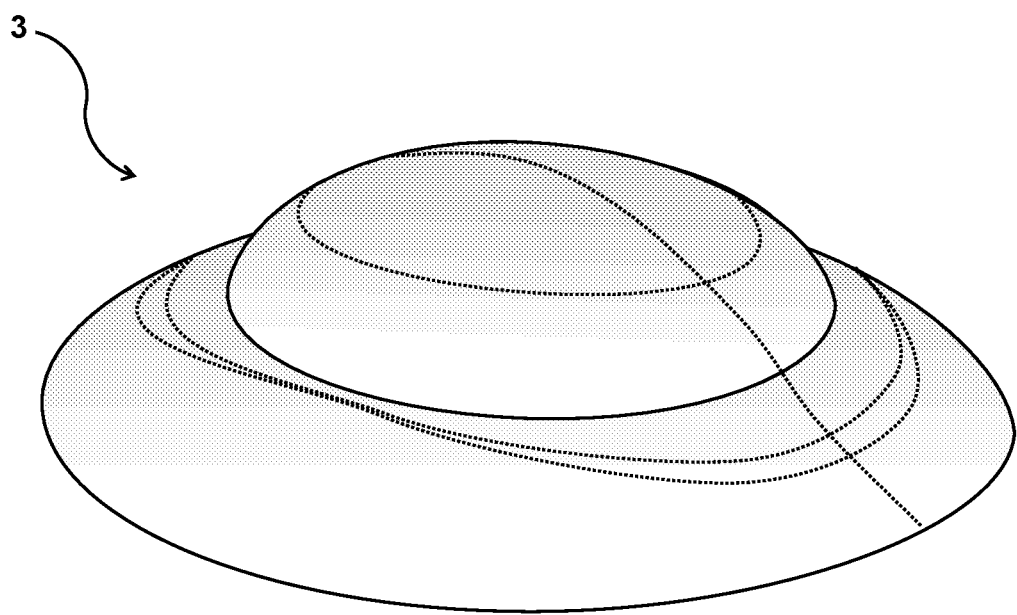
FIG. 4 illustrates the shape of a toric scleral lens.

FIG. 4 illustrates the shape of a toric scleral lens. This may provide further rotationally stability on the eye.

While the present systems and methods have been described in particular detail with reference to specific exemplary embodiments thereof, it should also be appreciated that numerous modifications and alternative embodiments may be devised by those having ordinary skill in the art without departing from the scope of the present disclosure. For example, embodiments wherein devices or systems are disclosed to be arranged and/or constructed for performing a specified method or function inherently disclose the method or function as such and/or in combination with other disclosed embodiments of methods or systems. Furthermore, embodiments of methods are considered to inherently disclose their implementation in respective hardware, where possible, in combination with other disclosed embodiments of methods or systems. Furthermore, methods that can be embodied as program instructions, e.g. on a non-transient computer-readable storage medium, are considered inherently disclosed as such embodiment.

Finally, the above-discussion is intended to be merely illustrative of the present systems and/or methods and should not be construed as limiting the appended claims to any particular embodiment or group of embodiments. The specification and drawings are accordingly to be regarded in an illustrative manner and are not intended to limit the scope of the appended claims. In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. The mere fact that certain measures are recited in mutually different claims does not indicate that a combination of these measures cannot be used to advantage. In particular, all working combinations of the claims are considered inherently disclosed.

The invention claimed is:

1. A method for measuring a subject's three dimensional eye movement including torsional rotation, the method comprising
    providing a contact lens placed over the subject's eye, wherein the contact lens comprises one or more markers that are positioned at a lateral offset with respect to a central part of the contact lens, which central part is positioned over a pupil of the subject's eye;
    using a video camera to track a position of the one or more markers;
    calculating an angle of the torsional rotation of the subject's eye around a line of sight axis of the subject's eye based on the tracked position of the one or more markers; and
    wherein the contact lens is painted with a ring-shaped opaque area surrounding a transparent central part, wherein the opaque area is disposed to partly cover an outside ring area of a subject's pupil to mask the outside ring area of the subject's pupil from the video camera to portray the subject's pupil with a constant shape and diameter to the video camera.

2. The method according to claim 1, wherein the one or more markers are formed in the opaque area.

3. The method according to claim 1, wherein a diameter of the transparent central part, defined by the surrounding ring-shaped opaque area, is less than four millimetres.

4. The method according to claim 1, wherein the angle of the torsional rotation is calculated by comparing a position of a marker to a position of a pupil of the subject's eye.

5. The method according to claim 1, wherein the video camera is an infrared camera having an infrared light source, wherein the one or more markers have more than eighty percent absorption in an infrared wavelength range of the infrared light source.

6. The method according to claim 1, wherein the one or more markers are formed by dark pigmented spots on a clear or contrasting background.

7. The method according to claim 1, wherein the one or more markers have a circular shape.

8. The method according to claim 1, wherein the one or more markers are isolated from each other and/or isolated from the pupil.

9. The method according to claim 1, wherein the one or more markers are disposed in a corneal area around the pupil of the subject's eye, in use overlapping an area of the subject's iris.

10. The method according to claim 1, wherein a pair of markers is positioned on a line at opposite sides of a central transparent part of the contact lens corresponding to the subject's pupil.

11. The method according to claim 1, wherein the contact lens is a scleral lens.

12. The method according to claim 1, wherein the contact lens is a toric scleral lens.

13. The method according to claim 1, comprising recording images of the subject's eye and calculating the angle of the torsional rotation based on a position of the one or more markers in the recorded images.

14. A system for measuring a subject's three dimensional eye movement including torsional rotation, the system comprising
    a contact lens for placement over the subject's eye, wherein the contact lens is painted with a ring-shaped opaque area surrounding a transparent central part, wherein the contact lens comprises one or more markers that are positioned at a lateral offset with respect to the transparent central part of the contact lens, which transparent central part is in use positioned over a pupil of the subject's eye, wherein the ring-shaped opaque area is disposed to partly cover an outside ring area of a subject's pupil to mask the outside ring area of the subject's pupil and portray the subject's pupil with a constant shape and diameter; and
    a non-transitory computer-readable medium with instructions which, when carried out on a computer, cause the computer to
        process video images of the contact lens to track a position of the one or more markers, and
        calculate an angle of the torsional rotation of the subject's eye around a line of sight axis of the subject's eye based on the tracked position of the one or more markers.

15. A contact lens for measuring a subject's three dimensional eye movement including torsional rotation, wherein the contact lens is configured for placement over the subject's eye, wherein the contact lens is painted with a ring-shaped opaque area surrounding a transparent central part, wherein the contact lens comprises one or more markers that are positioned at a lateral offset with respect to the transparent central part of the contact lens, which transparent central part is in use positioned over a pupil of the subject's eye, wherein the one or more markers are formed by dark pigmented circular spots on a contrasting background of the ring-shaped opaque area, wherein a diameter of the transparent central part, defined by the surrounding ring-shaped opaque area, is less than four millimeters to mask the outside ring area of the subject's pupil and portray the subject's pupil with a constant shape and diameter.

16. The contact lens according to claim 15, wherein a pair of the markers is positioned on a line at opposite sides of the transparent central part of the contact lens corresponding to the subject's pupil.

17. The contact lens according to claim 15, wherein the contact lens is a toric scleral lens.

\* \* \* \* \*